United States Patent
Lyndon et al.

(10) Patent No.: US 11,464,247 B2
(45) Date of Patent: Oct. 11, 2022

(54) SWEETENING COMPOSITIONS AND PROCESSES FOR PREPARING THEM

(71) Applicant: GUILIN GFS MONK FRUIT CORP., Guangxi (CN)

(72) Inventors: Rex Murray Lyndon, Paeroa (NZ); Christopher John Miller, Guangxi (CN); Garth Selwyn Smith, Guangxi (CN); Lan Fusheng, Auckland (NZ)

(73) Assignee: GUILIN GFS MONK FRUIT CORP., Guangxi (CN)

( * ) Notice: Subject to any disclaimer, the term of this patent is extended or adjusted under 35 U.S.C. 154(b) by 21 days.

(21) Appl. No.: 16/442,405

(22) Filed: Jun. 14, 2019

(65) Prior Publication Data

US 2020/0138063 A1   May 7, 2020

Related U.S. Application Data

(60) Continuation of application No. 14/685,507, filed on Apr. 13, 2015, now abandoned, which is a division of application No. 12/310,517, filed as application No. PCT/NZ2007/000263 on Sep. 7, 2007, now abandoned.

(51) Int. Cl.
| | | |
|---|---|---|
| A23L 27/30 | (2016.01) | |
| A23L 29/30 | (2016.01) | |
| C07J 17/00 | (2006.01) | |
| A23L 5/00 | (2016.01) | |
| A23L 2/60 | (2006.01) | |

(52) U.S. Cl.
CPC ............... *A23L 5/00* (2016.08); *A23L 2/60* (2013.01); *A23L 27/36* (2016.08); *A23L 29/30* (2016.08); *C07J 17/005* (2013.01); *A23V 2002/00* (2013.01)

(58) Field of Classification Search
CPC .. A23L 2/60; A23L 27/36; A23L 29/30; C07J 17/005
See application file for complete search history.

(56) References Cited

U.S. PATENT DOCUMENTS

| | | | |
|---|---|---|---|
| 2,388,194 | A | 10/1945 | Vallez |
| 2,926,110 | A | 2/1960 | Hiroshi et al. |
| 3,437,491 | A | 4/1969 | Peterson et al. |
| 4,775,541 | A | 10/1988 | Brown et al. |
| 5,411,755 | A | 5/1995 | Downton et al. |
| 5,419,251 | A | 5/1995 | Mantius et al. |
| 5,433,965 | A | 7/1995 | Fischer et al. |
| 6,124,442 | A | 9/2000 | Zhou et al. |
| 6,461,659 | B1 | 10/2002 | Zhou |
| 8,449,933 | B2 | 5/2013 | Ekanayake et al. |
| 2003/0165603 | A1 | 9/2003 | Burklow et al. |
| 2006/0003053 | A1 | 1/2006 | Ekanayake et al. |
| 2008/0075824 | A1 | 3/2008 | Biehl |
| 2008/0299277 | A1 | 12/2008 | Chao et al. |
| 2009/0092690 | A1 | 4/2009 | Yang et al. |
| 2009/0196966 | A1 | 8/2009 | West et al. |
| 2009/0311404 | A1 | 12/2009 | West et al. |
| 2010/0092638 | A1 | 4/2010 | Hansen et al. |
| 2010/0285197 | A1 | 11/2010 | Fisher et al. |
| 2011/0021456 | A1 | 1/2011 | Lyndon et al. |
| 2011/0200712 | A1 | 8/2011 | Takaichi |
| 2014/0044843 | A1 | 2/2014 | Lyndon |
| 2015/0216209 | A1 | 8/2015 | Lyndon et al. |
| 2016/0235098 | A1 | 8/2016 | Cox |
| 2018/0000140 | A1 | 1/2018 | Lyndon |
| 2019/0230965 | A1 | 8/2019 | Lan et al. |
| 2021/0282440 | A1 | 9/2021 | Lyndon |

FOREIGN PATENT DOCUMENTS

| | | |
|---|---|---|
| CN | 87101850 A | 12/1987 |
| CN | 1015264 B | 1/1992 |
| CN | 1019935 C | 2/1993 |
| CN | 1244531 A | 2/2000 |
| CN | 1259519 A | 7/2000 |
| CN | 1375499 A | 10/2002 |
| CN | 1508139 A | 6/2004 |
| CN | 1556110 A | 12/2004 |
| CN | 1600179 A | 3/2005 |
| CN | 1618335 A | 5/2005 |
| CN | 1620883 A | 6/2005 |

(Continued)

OTHER PUBLICATIONS

Abrams, I.M., Dickinson, B.N. 1949. "Color Removal in Sugar Liquors by Synthetic Resins." Industrial and Engineering Chemistry. vol. 41, pp. 2521-2523.*

Extended European Search Report received for European Patent Application No. 17863694.0, dated May 6, 2020, 9 Pages.

Final Office Action received for U.S. Appl. No. 14/685,507, dated Oct. 11, 2019, 11 pages.

Final Office Action received for U.S. Appl. No. 15/434,834, dated Sep. 23, 2019, 12 pages.

Search Report received for Chinese Patent Application No. 20178004792 dated Jan. 28, 2021, 6 pages (English translation pp. 1-3, Official copy pp. 4-6).

Advisory Action received for U.S. Appl. No. 12/310,517, dated May 16, 2014, 3 pages.

(Continued)

*Primary Examiner* — Nikki H. Dees
(74) *Attorney, Agent, or Firm* — Morrison & Foerster LLP

(57) ABSTRACT

The invention relates to sweetening compositions obtained from the Luo Han Guo fruit, a member of the Cucurbiticeae family. The compositions are free of bitter-tasting impurities, have a light colour and contain about 16-75% mogroside V and about 30-95% total terpene glycosides on a dry weight basis. A filtered (0.2 μm) solution of the composition in water with a solids content of 1% w/v has an absorbance at 420 nm of about 0.55 or below. Also disclosed is a method of preparing such compositions which includes a heating step to encourage the formation of melanoidins, highly coloured impurities, thereby permitting their removal by filtration providing a lighter coloured product.

17 Claims, No Drawings

(56) References Cited

FOREIGN PATENT DOCUMENTS

| | | | |
|---|---|---|---|
| CN | 1634814 A | 7/2005 |
| CN | 1663469 A | 9/2005 |
| CN | 1663474 A | 9/2005 |
| CN | 1683387 A | 10/2005 |
| CN | 1706861 A | 12/2005 |
| CN | 1723981 A | 1/2006 |
| CN | 1733130 A | 2/2006 |
| CN | 1733754 A | 2/2006 |
| CN | 1733785 A | 2/2006 |
| CN | 1733795 A | 2/2006 |
| CN | 1854149 A | 11/2006 |
| CN | 1872133 A | 12/2006 |
| CN | 1907091 A | 2/2007 |
| CN | 1303914 C | 3/2007 |
| CN | 101006849 A | 8/2007 |
| CN | 101007042 A | 8/2007 |
| CN | 100336822 C | 9/2007 |
| CN | 101029088 A | 9/2007 |
| CN | 101054384 A | 10/2007 |
| CN | 101057878 A | 10/2007 |
| CN | 100348610 C | 11/2007 |
| CN | 101096693 A | 1/2008 |
| CN | 101104628 A | 1/2008 |
| CN | 100382723 C | 4/2008 |
| CN | 101182286 A | 5/2008 |
| CN | 100391495 C | 6/2008 |
| CN | 101200753 A | 6/2008 |
| CN | 101228843 A | 7/2008 |
| CN | 100425605 C | 10/2008 |
| CN | 101283764 A | 10/2008 |
| CN | 101283831 A | 10/2008 |
| CN | 101285027 A | 10/2008 |
| CN | 101386636 A | 3/2009 |
| CN | 101402665 A | 4/2009 |
| CN | 101407535 A | 4/2009 |
| CN | 100491381 C | 5/2009 |
| CN | 101433592 A | 5/2009 |
| CN | 101434608 A | 5/2009 |
| CN | 101434636 A | 5/2009 |
| CN | 100513426 C | 7/2009 |
| CN | 101502313 A | 8/2009 |
| CN | 101522058 A | 9/2009 |
| CN | 100572552 C | 12/2009 |
| CN | 100589813 C | 2/2010 |
| CN | 101096693 B | 4/2010 |
| CN | 101690573 A | 4/2010 |
| CN | 101006849 B | 5/2010 |
| CN | 101007042 B | 5/2010 |
| CN | 101708249 A | 5/2010 |
| CN | 101711823 A | 5/2010 |
| CN | 101816790 A | 9/2010 |
| CN | 101120653 B | 10/2010 |
| CN | 101228843 B | 10/2010 |
| CN | 101708249 B | 10/2010 |
| CN | 101402665 B | 12/2010 |
| CN | 101711823 B | 12/2010 |
| CN | 101946887 A | 1/2011 |
| CN | 101948340 A | 1/2011 |
| CN | 101948501 A | 1/2011 |
| CN | 101973853 A | 2/2011 |
| CN | 101434608 B | 4/2011 |
| CN | 101386636 B | 5/2011 |
| CN | 101407535 B | 5/2011 |
| CN | 102048791 A | 5/2011 |
| CN | 102048857 A | 5/2011 |
| CN | 102050707 A | 5/2011 |
| CN | 102050848 A | 5/2011 |
| CN | 102058727 A | 5/2011 |
| CN | 101249130 B | 6/2011 |
| CN | 101433592 B | 6/2011 |
| CN | 101434636 B | 6/2011 |
| CN | 102084982 A | 6/2011 |
| CN | 102100394 A | 6/2011 |
| CN | 102125248 A | 7/2011 |
| CN | 102125249 A | 7/2011 |
| CN | 102180913 A | 9/2011 |
| CN | 102742801 A | 10/2012 |
| CN | 103145869 A | 6/2013 |
| CN | 103652776 A | 3/2014 |
| CN | 104086614 A | 10/2014 |
| CN | 104530168 A | 4/2015 |
| CN | 104558088 A | 4/2015 |
| CN | 106028835 A | 10/2016 |
| EP | 0229520 A1 | 7/1987 |
| EP | 2090181 A1 | 8/2009 |
| EP | 2190854 B1 | 11/2011 |
| EP | 2397485 A1 | 12/2011 |
| EP | 2882301 B1 | 9/2016 |
| JP | 56-158072 A | 12/1981 |
| JP | 58-71868 A | 4/1983 |
| JP | 9-234016 A | 9/1997 |
| JP | 2001-211854 A | 8/2001 |
| JP | 2010-502213 A | 1/2010 |
| JP | 2014-36678 A | 2/2014 |
| WO | 2006/005011 A1 | 1/2006 |
| WO | 2008/030121 A1 | 3/2008 |
| WO | 2008/102137 A1 | 8/2008 |
| WO | 2008/129457 A1 | 10/2008 |
| WO | 2009/038978 A2 | 3/2009 |
| WO | 2011/066754 A1 | 6/2011 |
| WO | WO-2012088169 A1 | 6/2012 |
| WO | 2018/077140 A1 | 5/2018 |

OTHER PUBLICATIONS

Aldrich, "Ion Exchange Resins: Classification and Properties", May 2018, pp. 28-30.

Brands et al., "Quantification of Melanoidin Concentration in Sugar-Casein Systems", Journal of Agricultural and Food Chemistry, vol. 50, No. 5, 2002, pp. 1178-1183.

Davis, SB, "The Chemistry of Colour Removal: A Processing Perspective", Proc S Afr Sug Technol Ass, vol. 75, 2001, pp. 328-336.

"Dow Liquid Separations. DOWEX Ion Exchange Resins. Juice Enhancement by Ion Exchange and Adsorbent Technologies.", Edited by: P. R. Ashurst, 7 pages.

Extended European Search Report received for European Patent Application No. 16189800.2, dated Dec. 16, 2016, 5 pages.

Final Office Action received for U.S. Appl. No. 12/310,517, dated Dec. 11, 2015, 19 pages.

Final Office Action received for U.S. Appl. No. 12/310,517, dated Mar. 11, 2014, 9 pages.

Final Office Action received for U.S. Appl. No. 13/961,763, dated Aug. 18, 2016, 12 pages.

Final Office Action received for U.S. Appl. No. 13/961,763, dated Oct. 8, 2014, 10 pages.

Final Office Action received for U.S. Appl. No. 14/685,507, dated May 18, 2018, 14 pages.

Galletti, Carl J., "Just the Facts: Knowing Strong Base Anion Resin Types", Available online at <https://www.wwdmag.com/just-facts-knowing-strong-base-anion-resin-types>, Dec. 28, 2000, 4 pages.

Harland, C E., "Ion Exchange Theory and Practice", 2nd Edition, Royal Society of Chemistry, 1994, pp. 59 and 63.

International Preliminary Report on Patentability received for PCT Patent Application No. PCT/CN2017/107363, dated May 9, 2019, 5 pages.

International Preliminary Report on Patentability received for PCT Patent Application No. PCT/NZ2007/000263, completed on Dec. 11, 2008, 11 pages.

International Preliminary Report on Patentability received for PCT Patent Application No. PCT/US2013/054007, dated Feb. 19, 2015, 6 pages.

International Search Report and Written Opinion received for PCT Patent Application No. PCT/CN2017/107363, dated Jan. 18, 2018, 6 pages.

International Search Report and Written Opinion received for PCT Patent Application No. PCT/NZ2007/000263, dated Jan. 15, 2008, 10 pages.

(56) References Cited

OTHER PUBLICATIONS

International Search Report received for PCT Patent Application No. PCT/US2013/054007, dated Sep. 26, 2013, 3 pages.
International Written Opinion received for PCT Patent Application No. PCT/US2013/054007, dated Sep. 26, 2013, 5 pages.
Lee, Chi-Hang, "Intense sweetener from Lo Han Kuo (*Momordica grosvenori*)", Experentia, vol. 31, No. 5, Oct. 17, 1974, pp. 533-534.
Liu, Zhongdong, "Extraction and Purification of Mogroside (V)", Ion Exchange and Adsorption, vol. 15, No. 4, 1999, pp. 364-368.
Madhavan, R., "Optimization Liquid-Liquid Extraction", Chemical Engineering Tools and Information, Feb. 2001, pp. 1-12.
Matsumoto et al., "Minor Cucurbitane-Glycosides from Fruits of Siraitia grosvenori (Cucurbitaceae)", Chemical and Pharmaceutical Bulletin, vol. 38, No. 7, 1990, pp. 2030-2032.
Morris, Manning & Martin, LLP, "Explanation of Qin Benjun, et al and Yu Lijuan et al Documents", pp. 1-13.
Non-Final Office Action received for U.S. Appl. No. 12/310,517, dated Jul. 3, 2012, 8 pages.
Non-Final Office Action received for U.S. Appl. No. 12/310,517, dated Sep. 23, 2013, 8 pages.
Non-Final Office Action received for U.S. Appl. No. 13/961,763, dated Feb. 10, 2014, 14 pages.
Non-Final Office Action received for U.S. Appl. No. 13/961,763, dated Jan. 12, 2016, 11 pages.
Non-Final Office Action received for U.S. Appl. No. 15/434,834, dated Jan. 18, 2019, 11 pages.
Non-Final Office Action received for U.S. Appl. No. 12/310,517, dated Jan. 13, 2015, 9 pages.
Non-Final Office Action received for U.S. Appl. No. 14/685,507, dated Aug. 15, 2017, 12 pages.
Non-Final Office Action received for U.S. Appl. No. 14/685,507, dated Dec. 13, 2016, 15 pages.
Norit, "Norit Novelties in Sugar & Sweetener Purification", Know How Magazine, No. 1, 2005, pp. 1-2.
Puretec, "Basics of Deionized Water by Ion Exchange", Available Online at <https://puretecwater.com/downloads/basics-of-ion-exchange.pdf>, 2 pages.
Rohm and Haas, "Ion Exchange for Dummies", Available online at <http://www.lenntech.com/Data-sheets/Ion-Exchange-for-Dummies-RH.pdf>, Sep. 2008, pp. 1-9.
Extended European Search Report received for European Patent Application No. 07834865.3, dated Jun. 10, 2010, 8 pages.
Takemoto et al., "Studies on the Constituents of Fructus Momordicae. III. Structure of Mogrosides", Yakugaku Zasshi, vol. 103, No. 11, 1983, pp. 1167-1173.
Tang et al., "Chemical Constituents of Momordica Grosvenori", Chinese Drugs of Plant Origin: Chemistry, Pharmacology, and Use in Traditional and Modern Medicine, vol. 21, No. 6, 1992, 2 pages.
Wheaton et al., "Fundamentals of Ion Exchange", Dowex Ion Exchange Resins, Jun. 2000, 9 pages.
Yoshikawa et al., "Transglycosylation of Mogroside V, A Triterpene Glycoside in Siraitia Grosvenori, by Cyclodextrin Glucanotransferase and Improvement of the Qualities of Sweetness", J. Appl. Glycosci., vol. 52, 2005, pp. 247-252.
Yu et al., "Preparation of Mogroside V from Fresh Fruits of Luohanguo by High Performance Liquid chromatography", Chinese Journal of Chromatography, vol. 21, No. 4, Jul. 2003, pp. 397-399.
Yu et al., (2014). "Chapter 12: Saccharides," Medical Chemistry, Huazhong University of Science & Technology Press, p. 123, 4 pages.

* cited by examiner

SWEETENING COMPOSITIONS AND PROCESSES FOR PREPARING THEM

CROSS-REFERENCE TO RELATED APPLICATIONS

This application is a continuation application of U.S. patent application Ser. No. 14/685,507, filed Apr. 13, 2015, which is a Divisional of U.S. patent application Ser. No. 12/310,517, which is a National Phase of International Application of PCT/NZ2007/000263, filed Sep. 7, 2007, which claims priority to and the benefit of New Zealand Patent Application No. 549739, filed Sep. 7, 2006, the disclosures of which are hereby incorporated by reference herein.

FIELD OF THE INVENTION

This invention relates to sweetening compositions. It more particularly relates to sweetening compositions containing terpene glycosides, and to foods and beverages sweetened with such compositions. The invention also relates to processes for preparing the sweetening compositions.

BACKGROUND OF THE INVENTION

With obesity on the rise in the Western world, consumers are constantly looking for ways to reduce the calorie content of their diet, but without sacrificing flavour. Many lower calorie food and beverage products have been developed. There are a number of low calorie products containing artificial non-nutritive sweeteners, such as saccharine, aspartame, cyclamate, dipeptides, trichlorosucrose and Acesulfame K. However, there is growing concern over the safety of some of these artificial sweeteners and many consumers would prefer to reduce their intake of such sweeteners.

Certain naturally-occurring terpene glycosides, particularly triterpene glycosides, are both intensely sweet and non-calorific. For these reasons, triterpene glycosides are very attractive for use as a sweetening agent in the food, beverage and dietary industries.

Luo Han Guo refers to the fruit of *Siraitia grosvenorii* (formerly known as *Momordica grosvenoriz*), a member of the Cucurbitaceae family. Luo Han Guo is grown in the South East provinces of China, mainly in the Guangxi region. It has been cultivated and used for hundreds of years as a traditional Chinese medicine to treat coughs and congestion of the lungs, and also as a sweetener and flavouring agent in soups and teas.

Luo Han Guo and other fruit of the Cucurbitaceae family contain terpene glycosides known as mogrosides and siamenosides, which are present at a level of around 1% of the fleshy part of the fruit. These compounds have been described and characterized by Matsumoto et al; *Chem. Pharm. Bull.*, 38(7), 2030-2032 (1990). Mogrosides are compounds in which between one and six glucose molecules are attached to a triterpene backbone. The most abundant mogroside is mogroside V, which has been estimated to have a sweetness of approximately 250% of that of cane sugar, on a weight basis.

The Luo Han Guo fruit itself, although sweet, is unsuitable for widespread use as a non-nutritive sweetener without additional processing. The raw fruit has a tendency to easily form off-flavours by fermentation. Also, its pectin eventually gels. Drying the fruit preserves it, but also causes the formation of other undesirable bitter, astringent and cooked flavours. A number of methods have been described for processing Luo Han Guo to remove undesired flavour components, to produce extracts containing mogrosides, that have a flavour profile more acceptable for use as sweetening compositions.

*Experientia* 31(5) 533-534, 1975 (Lee, C. H.) describes a process for extracting mogrosides from Luo Han Guo using hot water extraction, followed by passing the extract containing mogrosides through an Amberlite resin that retains the mogrosides, and eluting the mogrosides with 50% ethanol.

U.S. Pat. No. 5,411,755 describes a process for preparing a sweet juice containing mogrosides and sugar from Luo Han Guo fruit. The process involves separating peel and seeds from unprocessed juice of the fruit, acidifying the juice, removing off-flavour precursors from the fruit, and removing a methylene chloride extractable volatiles fraction from the juice.

U.S. Pat. No. 5,433,965 describes a sweetener composition comprising a combination of sugar and a sweet juice containing mogrosides derived from Luo Han Guo fruit.

U.S. patent application Ser. No. 10/086,322 describes a sweetener blend composition comprising Luo Han Guo fruit concentrate, fructose and maltodextrin.

U.S. Pat. No. 6,124,442 describes a process for preparing a dry composition containing mogrosides and derived from Luo Han Guo fruit. The process includes obtaining a liquid extract from Luo Han Guo and mixing the extract with a solution saturated with at least one element having an oxidation number of one or two. The resulting mixture provides for a solid precipitate material and a liquid portion containing the triterpene glycosides which is then passed through a macroporous resin. The resin is then washed with an alcohol to obtain a solution thereof containing the triterpene glycosides. The solution is condensed to provide a purified liquid triterpene glycoside solution and then a drying step is performed to obtain a dry composition containing the triterpene glycosides.

U.S. patent application publication 20060003053A1 describes a process for extracting juice from a plant material containing triterpene glycosides. The process involves the steps of crushing the plant material, blanching the crushed plant material in acidified water to obtain a puree comprising a juice extract and a plant solids residue, separating the juice extract from the plant solids residue, mixing an enzyme with the juice extract and separating the juice extract to obtain a sweet juice.

Chinese patent 1015264 describes a process for preparing a dry composition containing mogrosides and derived from Luo Han Guo fruit. The process includes obtaining a liquid extract from Luo Han Guo using water at a temperature of 50-60° C., contacting the liquid extract with an adsorbent resin to concentrate mogrosides, eluting mogrosides with ethyl alcohol, decolourising the extract with an ion exchange resin, then recovering the alcohol post decolourising and finally freeze drying.

Despite advances in processing technology, existing sweetening compositions derived from Luo Han Guo fruit still suffer from the disadvantages of having a brown/yellow colour and noticeable undesirable flavours.

Thus there remains a need for sweetening compositions containing terpene glycosides that have a clean flavour with minimal undesirable or "off" notes and and light colour. It is an object of the present invention to go at least some way towards providing such a composition or at least to provide the public with a useful choice.

SUMMARY OF THE INVENTION

In a first aspect, the present invention provides a sweetening composition, the composition containing from about 16% to about 75% mogroside V and from about 30% to about 95% total terpene glycosides on a dry weight basis, and wherein a filtered (0.2 µm) solution of the composition in water having a solids content of 1% w/v has an absorbance at 420 nm of about 0.55 or below.

In a preferred embodiment, the composition is in the form of a powder. In another embodiment, the composition is in the form of a liquid, conveniently an aqueous solution.

Preferably, the terpene glycosides in the composition are naturally occurring terpene glycosides obtained from fruit of the Cucurbitaceae family.

Preferably the terpene glycosides in the composition are triterpene glycosides obtained from Luo Han Guo fruit.

More preferably, substantially all of the solid components of the composition are obtained from Luo Han Guo fruit.

In preferred embodiments, the composition contains from about 20% to about 70% mogroside V and from about 40% to about 90% total terpene glycosides, such as about 30% to about 65% mogroside V and about 50% to about 85% total terpene glycosides, such as about 35% to about 60% mogroside V and about 55% to about 85% total terpene glycosides, such as about 40% to about 55%, mogroside V and about 60% to about 80% total terpene glycosides, on a dry weight basis.

In preferred embodiments, the absorbance at 420 nm of a filtered (0.2 µm) solution of the composition in water having a solids content of 1% w/v is less than about 0.5, more preferably less than about 0.4, such as less than about 0.35, such as less than about 0.3, such as from about 0.05 to about 0.25.

In a further aspect, the present invention provides a sweetening composition comprising:
 (a) a first component containing from about 16% to about 75% mogroside V and from about 30% to about 95% total terpene glycosides on a dry weight basis, and wherein a filtered solution (0.2 µm) of the first component in water having a solids content of 1% w/v has an absorbance at 420 nm of about 0.55 or below; and
 (b) one or more additional components.

The additional components may be selected from colouring agents, flavouring agents and other sweetening agents.

In preferred embodiments, substantially all of the solid components of the first component are derived from fruit of the Cucurbitaceae family, preferably Luo Han Guo fruit.

In a further aspect, the invention provides a beverage containing a sweetening composition of the invention as described above.

In a further aspect, the invention provides a food product containing a sweetening composition of the invention as described above.

In a further aspect, the invention provides a healthcare composition comprising a sweetening composition of the invention as described above.

In a further aspect, the invention provides a process of preparing a sweetening composition containing terpene glycosides, the process comprising the following steps:
 (a) obtaining a terpene glycoside-containing liquid extract from a fresh plant source material containing terpene glycosides;
 (b) clarifying the extract;
 (c) concentrating terpene glycosides in the extract to obtain a purified terpene glycoside-containing solution;
 (d) heating the purified terpene glycoside-containing solution to a sufficient temperature and for a sufficient time to form melanoidins; and
 (e) separating melanoidins from terpene glycosides in the solution to obtain a decolourised terpene glycoside-containing solution.

In preferred embodiments, the process also includes the step of drying the decolourised terpene glycoside-containing solution obtained from step (e) to form a powdered composition. In preferred embodiments, the decolourised terpene glycoside-containing solution obtained from step (e) is first concentrated before final drying.

In preferred embodiments, the fresh plant source material is a fruit of the Cucurbitaceae family, more preferably Luo Han Guo.

In preferred embodiments, step (a) comprises contacting macerated Luo Han Guo fruit with hot water, at a sufficient time and for a sufficient temperature to extract triterpene glycosides from the fruit. In particularly preferred embodiments, the contacting is carried out using countercurrent extraction.

In preferred embodiments, the clarification step (b) comprises ultrafiltration of the extract.

In alternative embodiments, step (b) comprises treating the extract with a pectinase enzyme (preferably a commercial pectinase preparation) under conditions which lyse pectins and complex saccharides facilitating clarification.

In preferred embodiments, the liquid extract obtained from step (b) is filtered, centrifuged or decanted before step (c).

In preferred embodiments, the step (c) of concentrating terpene glycosides comprises (i) contacting the clarified extract with an adsorbent resin, wherein the adsorbent resin binds terpene glycosides in the extract; and (ii) eluting terpene glycosides from the resin to obtain a purified terpene glycoside-containing solution.

In preferred embodiments, the adsorbent resin used in step (c) is a macroporous polymeric adsorbent resin, such as a styrene divinylbenzene copolymer, or divinylbenzene copolymer resin.

In preferred embodiments, step (c) is carried out in a pressurised vessel.

In preferred embodiments, in step (c) the terpene glycosides are eluted from the adsorbent resin with an aqueous solution of ethanol. In particularly preferred embodiments, the elution is carried out using a plurality of elution steps using ethanol solutions of increasing ethanol concentration.

In preferred embodiments, the heating step (d) comprises heating the terpene-glycoside containing ethanol solution(s) obtained from step (c), to both promote formation of melanoidins and evaporate ethanol, thereby allowing recovery of the ethanol.

In preferred embodiments, step (d) comprises heating the purified terpene glycoside-containing solution to a temperature of about 80° C. to about 120° C., for a period of time sufficient to form melanoidins.

In certain embodiments, the heating is carried out at a temperature of about 80° C. to about 100° C., for a time of about 120 minutes to about 45 minutes.

In preferred embodiments, the decolourising step (e) comprises contacting the terpene glycoside and melanoidin-containing solution from step (d) with a decolourising resin which binds the melanoidins (and optionally other non-terpene glycoside molecules), to obtain a decolourised terpene glycoside-containing solution.

In preferred embodiments, the decolourising resin used in step (e) comprises a highly porous, macroporous, type I, strongly basic anion resin, preferably regenerated in the chloride form.

In preferred embodiments, step (e) is carried out in a pressurised vessel.

In a further aspect, the present invention provides a process of preparing a sweetening composition from a fresh plant source material containing terpene glycosides, characterized in that the process includes the steps of:
  (a) heating a terpene glycoside-containing solution obtained by extracting terpene glycosides from the plant source material, to a sufficient temperature and for a sufficient time to form melanoidins; and
  (b) separating the melanoidins from the terpene glycosides in the extract to obtain a decolourised terpene glycoside-containing solution.

In preferred embodiments, the terpene glycoside-containing solution used in step (a) is obtained by an extraction process comprising the steps of contacting macerated Luo Han Guo fruit with hot water, at a sufficient time and for a sufficient temperature to extract triterpene glycosides from the fruit, followed by clarification of the solution.

In particularly preferred embodiments, the contacting is carried out using countercurrent extraction.

In particularly preferred embodiments, the clarification step comprises ultrafiltration of the extract.

In preferred embodiments, step (b) comprises contacting the resulting terpene glycoside- and melanoidin-containing solution with a decolourising resin that binds melanoidins (and optionally other non-terpene glycoside molecules in the solution).

In preferred embodiments, the process includes the step of concentrating terpene glycosides in the solution. Preferably this step comprises (i) contacting the clarified extract with an adsorbent resin, wherein the adsorbent resin binds terpene glycosides in the extract; and (ii) eluting terpene glycosides from the resin to obtain a purified terpene glycoside-containing solution.

In preferred embodiments, the adsorbent resin used in the concentration step is a macroporous polymeric adsorbent resin, such as a styrene divinylbenzene copolymer, or divinylbenzene copolymer resin.

In preferred embodiments the process includes the step of drying the decolourised terpene glycoside-containing solution obtained from step (b) to form a powdered composition.

In a further aspect, the invention provides a sweetening composition obtained by or obtainable by a process as described above.

In a further aspect, the invention provides a food product or a beverage containing a sweetening composition obtained by or obtainable by a process as described above.

Although the invention is broadly as defined above, it is not limited thereto and also includes embodiments of which the following description provides examples.

DETAILED DESCRIPTION OF THE INVENTION

Definition

In this specification, unless the context requires otherwise, the term "total terpene glycosides" means the total concentration of terpene glycosides determined in a composition based on the accrual of individual terpene glycoside peaks observed during an HPLC analysis. Also, for the avoidance of doubt, the term "triterpene glycosides" includes without limitation both mogrosides and siamenosides.

Sweetening Compositions of the Invention

As defined above, the present invention relates to sweetening compositions containing terpene glycosides. The compositions are preferably derived from fruit of the Cucurbitaceae family, preferably Luo Han Guo fruit, containing triterpene glycosides (mogrosides and siamenosides). The sweetening compositions of the present invention, at least in preferred embodiments, have a cleaner flavour and lighter colour than existing sweetening compositions derived from Luo Han Guo.

In one aspect, then, the invention relates to a sweetening composition containing terpene glycosides, wherein a 0.2 μm filtered solution of the composition in water having a solids content of 1% w/v has an absorbance at 420 nm or about 0.55 or below. The proportions of terpene glycosides in the sweetening compositions of the present invention may vary, depending on the natural diversification of the fruit source material from which the composition is made. The compositions of the present invention generally contain between about 16% and about 75% mogroside V and between about 30% and about 95% total terpene glycosides, on a dry weight basis.

In certain preferred embodiments, the compositions of the invention may contain about 35% to about 60% mogroside V, and about 55% to about 85% total terpene glycosides on a dry weight basis.

As indicated above, the absorbance at 420 nm of a sub-micron (0.2 μm) filtered solution in water of the compositions of the present invention having a solids content of 1% w/v is about 0.55 or below. The absorbance at 420 nm correlates with the colour of the compositions—the lower the absorbance, the lighter the colour. Also, the applicants have found that the absorbance at 420 nm correlates with the caramelised, cooked and maple taste of the compositions—the lower the absorbance, the cleaner the flavour of the compositions. The compositions of the present invention have an off-white to pale yellow colour, and a clean flavour, with minimal liquorice and burnt-type caramel and maple flavours that are associated with prior art compositions.

Preferred compositions of the present invention include those in which the absorbance at 420 nm of a filtered (0.2 μm) solution of the composition in water having a solids content of 1% w/v has an absorbance of less than about 0.3, such as about 0.05 to about 0.25.

The compositions of the present invention may be in the form of either a liquid or solid. In particularly preferred embodiments, the compositions of the invention are in the form of a powder. In other embodiments, the compositions may be in the form of an aqueous solution.

In certain preferred embodiments, the compositions of the invention consist of, or consist essentially of, material naturally occurring in and extracted from fruit of the Cucurbitaceae family, preferably Luo Han Guo fruit, ie the compositions do not include significant proportions of solid components from sources other than Cucurbitaceae fruit. These compositions of the invention are non-nutritive, with the only sweetening components in the compositions being terpene glycosides.

In certain alternative embodiments, the sweetening compositions of the present invention may be combined with other materials, such as desired additional flavouring, colouring and/or sweetening agents. In another aspect, then, the invention relates to a sweetening composition comprising (a) as a first component, a composition of the present invention as described above, containing from about 16% to about 75% mogroside V and from about 30% to about 95% total terpene glycosides on a dry weight basis, and wherein a filtered solution (0.2 μm) of the first component in water having a solids content of 1% w/v has an absorbance at 420 nm of about 0.55 or below; and (b) one or more additional components.

In preferred embodiments, substantially all of the solid components of the first component are derived from fruit of the Cucurbitaceae family, preferably Luo Han Guo fruit.

The additional components may be selected from colouring agents, flavouring agents and other sweetening agents.

The compositions of the present invention may be used as sweetening agents in various foods, beverages and confectionery products.

Preparation of Sweetening Compositions of the Invention

Melanoidins are coloured compounds formed primarily by interactions between carbohydrates and compounds having a free amino group, such as free amino acids and the free amino groups of peptides and proteins. The complex network of interactions, resulting in melanoidins as the final reaction products, are commonly referred to as the Maillard reaction.

The applicants have surprisingly found that by incorporating into a process of extracting terpene glycosides from a plant source material such as Luo Han Guo, the step of heating a terpene glycoside-containing extract for a sufficient time and temperature to encourage the Maillard reaction and formation of melanoidins (from endogenous fruit carbohydrate and amino-group-containing impurities remaining in the extract), the coloured melanoidin compounds formed can thereafter be removed from the extract, conveniently using a decolourising step, furnishing a product having a clean flavour and light colour.

Processes of preparing the sweetening compositions of the present invention will now be described in more detail.

The sweetening compositions of the present invention can be made from any fruit of the family Cucurbitaceae, tribe Jollifieae, subtribe Thladianthinae, genus *Siraitia*, that contains sweet terpene glycosides. Such fruit include *S. grosvenorii, S. siamensis, S. silomaradjae, S. sikkimensis, S. africana, S. borneensis* and *S. taiwaniana*. It is however most preferred that the fruit used is *S. grosvenorii*, also referred to as Luo Han Guo fruit. The following description of the process is with reference to making sweetening compositions from Luo Han Guo fruit.

Luo Han Guo fruit is selected, stored and processed to provide a good quality starting material preferably with a high level of sweetness. Typically the fresh fruit is then mechanically shredded or crushed. The shredded or crushed fruit is then preferably contacted with hot water to extract mogrosides from the fruit. It is preferred that the extraction process includes a period immediately after the fruit is shredded or crushed when the temperature of the water is greater than about 60° C., preferably greater than about 80° C., sufficient to pasteurise the fruit and to inactivate endogenous enzymes (such as protease) present in the fruit. Inactivating the endogenous enzymes at this stage has the beneficial effect of reducing enzymatic browning and limiting off-flavour formation caused by enzymatic action. It is preferred that the fruit and water are well mixed to ensure even contact between the fruit and the hot water thus ensuring the enzymes are evenly exposed to the hot water and therefore denatured as quickly as possible.

For example, a continuous countercurrent extraction process can be used, whereby the shredded fruit is fed into the countercurrent extractor where it is contacted with water at approximately 80° C. for approximately 30 minutes. Countercurrent extraction processes and apparatus are known in the art. By way of example, a countercurrent extractor of the type described in U.S. Pat. No. 5,419,251 (Mantius et al), with or without the longitudinal members described, may be used in the processes of the present invention. One advantage of using a countercurrent extraction process is that the extraction times needed to extract substantially all of the available soluble solids are typically less than if a conventional pot-type extraction process was used. Generally, the contact time between the fruit and the water in a countercurrent extraction process is between about 30 and 60 minutes whereas to achieve the same extraction of soluble solids in a pot process may take 3 separate decoctions and require contact time of between 90 and 120 minutes. Another advantage is that less water is usually needed. Typically, a ratio of water to fruit of around 1.5:1 will suffice in a countercurrent extraction process, whereas in a pot-type multiple extraction process a water:fruit ratio of around 3:1 is generally required.

Alternatively, the water may be heated to about 100° C. and the mixture decocted for about 30 to 60 minutes, such as about 45 minutes. The decoction is then drained off the fruit and preferably filtered or screened to remove large fruit pulp particles. The hot water extraction process may be repeated one or more times on the fruit remaining, and the decoctions obtained from each extraction combined.

The decoction or liquid extract obtained is then preferably cooled, and clarified to provide clarity and prevent gelling of the juice. The clarification may be carried out using any suitable method.

In preferred embodiments, the clarification is carried out by use of ultrafiltration, such as by using an ultrafiltration membrane with a molecular weight cut-off that allows for the passage of the mogrosides in the permeate while retaining unwanted proteins and pectins in the retentate. An ultrafiltration membrane of between 50,000-100,000 daltons is therefore preferred.

Alternatively, the clarification may be carried out by treatment with phosphoric acid or with pectinase enzyme. Pectinase enzyme may be used conveniently in the form of a commercially available enzyme mixture containing pectinase enzyme, in order to lyse the pectin and precipitate pectin-stabilised peptides and protein from the liquid extract. Suitable commercially available enzyme preparations include Novozyme 3356 and Rohapect B1. Pectinase may be added as a dilute solution, in an amount of from about 0.001% to about 1%, on a dry weight basis. Conveniently the liquid extract is held with the pectinase with gentle agitation at a temperature of about 30° C. to about 55° C., such as about 40° C. to about 50° C., until the liquid extract is substantially free of pectin, typically for a period of about 15 to about 60 minutes, such as about 30 minutes.

The liquid extract is then preferably treated to deactivate the pectinase and to denature proteins improving coagulation and their co-precipitation with the degraded pectin. This may conveniently be achieved by heating rapidly to about 80° C. to about 90° C., such as to about 85° C., for a time sufficient to deactivate the pectinase, such as about 30 seconds to about 5 minutes.

Following deactivation of the pectinase plus coagulation and co-precipitation of the protein, the liquid extract is then preferably cooled sufficiently to allow it to be filtered easily to remove flock and denatured protein. The extract is typically cooled to less than about 65° C., more typically less than about 50° C. The filtration may be carried out using any convenient method known in the art, such as through diatomaceous earth, or by cross-flow ultra- or micro-filtration. It is preferred that the extract is filtered to optical clarity (less than 5 NTU).

The next stage is to concentrate triterpene glycosides from the clarified liquid extract. This may conveniently be achieved by contacting the liquid extract with an adsorbent resin that binds the triterpene glycosides. Adsorbent resins suitable for use to harvest triterpene glycosides include resins with a wettable hydrophobic matrix and that are suitable for contact with food, such as PVPP (polyvinylpolypyrrolidone), nylon, acrylic esters, styrene divinylbenzene copolymers, divinylbenzene copolymers, and activated carbon. Such resins are commercially available. Preferred resins suitable for use in the present invention are styrene divinylbenzene copolymers and divinylbenzene copolymers. An example of a preferred resin is a divinylbenzene copolymer resin known as Alimentech P470 and commercially available from Bucher-Alimentech Ltd. A preferred arrangement is to use at least 3 columns of resin operated in carousel mode. It is also preferred that this stage of the process is carried out in a pressurised vessel.

Following contacting of the liquid triterpene glycoside-containing extract with the adsorbent resin to harvest the mogrosides onto the resin, the bound triterpene glycosides are eluted from the resin using a suitable food grade solvent. For example, when the resin used is Alimentech P470, mogrosides may conveniently be eluted with successive increments of aqueous ethanol. By way of example, a suitable elution sequence may involve first displacing residual liquid Luo Han Guo extract by rinsing with water, then carrying out pre-elution resin swelling using first 10% then 20% v/v ethanol in water, followed by elution of triterpene glycosides using 35%, 42%, then 50% v/v ethanol in water and collection of the triterpene glycoside-rich mother liquor. The resin may conveniently be rejuvenated for re-use with a 80% v/v solution of ethanol in water followed by rinsing with water and adjustment of the pH as required. The solvent may be recovered by distillation for reuse.

The mother liquor (purified triterpene glycoside-containing solution) obtained from the adsorbent resin is subjected to a heating step, to encourage the formation of coloured melanoidins from residual protein and peptides in the mother liquor. The preferred heating temperature and time will depend on the residual levels of protein and peptides in the mother liquor, and also the pressure at which the heating step is carried out. The formation of melanoidins can be detected visually, as the solution will become browner in colour.

In general, suitable temperatures for allowing the development of melanoidins range from about 80° C. to about 120° C. The heating time required will depend on the factors mentioned above, and also the temperature at which the heating is carried out. However, preferred heating times may range from about 120 minutes to about 45 minutes, at about 80° C. to about 100° C., such as about 120 minutes to about 90 minutes at about 80° C. to about 90° C., if the heating is not carried out at elevated pressure. It will be appreciated that if the heating is carried out under elevated pressure, the time required for development of melanoidins will be reduced. For example, if the heating is carried out at a pressure of about 1 Bar gauge and at a temperature of about 120° C., a heating time of only about 10 minutes may be sufficient. On the other hand, if the heating is carried out at about 90° C. at atmospheric pressure, a heating time of up to about two hours may be required.

Conveniently, as well as promoting the development of melanoidins, the heating step (d) may also serve to evaporate some of the alcohol from the mother liquor, allowing recovery of ethanol from the mother liquor.

After the heating step, the mother liquor is preferably cooled rapidly, preferably to about ambient temperature, conveniently to less than about 30° C. The mother liquor is then subject to a decolourising step, to separate the terpene glycosides in the solution from the melanoidins, and also preferably from other non-terpene glycoside molecules. Conveniently, this may be achieved by contacting the mother liquor with a decolourising resin that adsorbs the coloured melanoidin compounds, and other non-terpene glycoside molecules in the solution. Suitable decolourising resins are known in the art and are commercially available. Highly porous, macroporous, type I, strongly basic anion resins, preferably regenerated in the chloride form, are examples of resins particularly suitable for use in the present invention. An example of one such resin is that known as Alimentech A330, commercially available from Bucher-Alimentech Limited.

The decolourising step may be carried out in a number of stages, incorporating inter-step pH adjustment, and using a number of chromatography columns, such as two or three columns, joined in sequence, or segmented in a single column. The A330 resin may be regenerated with caustic brine followed by rinsing with hardness free water. The mother liquor is pumped successively through the resin columns to allow binding of melanoidins to the resin. It will also be appreciated that other non-terpene glycoside components present in the mother liquor, such as proteins and flavones, will also bind to the decolourising resin. It is preferred that the arrangement allows for injection of a pH adjusting agent, such as dilute citric acid, into the resin columns, to maintain a pH of about 3.3 to about 4.3 in the mother liquor passing into the successive columns or column segments. It is also preferred that the pH of the decolourised triterpene glycoside-containing solution is then adjusted as required to about 4 or below, conveniently about 3.8, to inhibit colour reversion in the subsequent concentration and drying steps.

The decolourised triterpene glycoside-containing solution is then further processed to obtain a refined, bland tasting, pale coloured sweetener concentrate or a powder, as desired. The triterpene glycoside-containing solution is preferably first concentrated before drying. This may conveniently be carried out by any suitable method, for example using a spinning cone evaporator under vacuum, at a temperature of around 65° C. The resulting concentrated solution may then be dried using any suitable method known in the art, such as freeze-drying, vacuum-drying, spray-drying or in a forced air oven, at a temperature applicable to the method.

The process of the present invention may be employed on a commercial scale to make substantial quantities of sweetening compositions. It will also be appreciated that various batches of sweetening compositions of the present invention containing varying levels of triterpene glycosides may be blended together where a consistent composition having particular proportions of mogroside V and total triterpene glycosides is desired.

The invention will now be described in further detail with reference to the following non-limiting examples.

EXAMPLES

Examples 1, 2 and 3 below describe the preparation of three sweetening compositions according to the present invention, containing 54% w/w mogroside V, 39% w/w mogroside V, and 42% w/w mogroside V respectively. The percentages of mogroside V are on a dry weight basis, after drying for 2 hours at 85° C.

Example 1

Luo Han Guo fruit extract, (pH 4.2 and 6.2 w/w soluble solids by refractometer), was received frozen from Guilin, P R China. The Luo Han Guo extract had been prepared by the following method.

1.2 tonnes of good quality, fresh Luo Han fruit is mechanically shredded and dropped into a steam jacketed vat. 1,500 L of filtered water is added to the macerated fruit. The water is heated to 100° C. and the mixture is decocted for 45 minutes. After 45 minutes the decoction is drained off the fruit and filtered to remove large fruit particles. A further 1,500 L of water is added to the fruit remaining in the vat. The water is heated to 100° C. and the mixture is decocted for 45 minutes. After 45 minutes the decoction is drained off the fruit, filtered to remove large fruit particles, and combined with the decoction from the first cycle. This cycle is repeated one more time to give a total volume of 4,500 L of supernatant. The supernatant has soluble solids of between 3%-6.5%.

The extract was thawed and 988 g warmed in a thermostatically controlled water bath to 45±5° C.

1. Removal of suspended solids to avert blinding of the harvesting adsorbent resin.

A proprietary pectinase enzyme preparation (Novozym 3XL) 0.2 mL was added and the mixture gently stirred for 30 minutes until a flock formed and began to settle, whereupon the temperature was rapidly raised to 85° C. to terminate the enzyme activity plus held at 85° C. for an additional 5 minutes to denature labile indigenous fruit proteins. Thereafter the separating mixture was cooled sufficiently (to <50° C.) for ease of filtration through diatomaceous earth (Celite filtercel) under vacuum, (20-30 mm Hg), yielding material, pH 4.4 and 6.1% w/w soluble solids, Absorbance$_{420}$ 1.006, of optically bright golden brown liquid turbidity <5 NTU, (nephelometric turbidity units).

2. Concentration of mogrosides by harvesting onto Alimentech P470 US-FDA compliant adsorbent resin.

Commercially available divinylbenzene copolymer adsorbent resin, (Alimentech P470), was prepared for contact with food as defined in US FDA 21 CFR Ch. 1, 173.65, by following the supplier's (Bucher-Alimentech Ltd) instructions. 100 mL of the prepared resin was packed in a glass chromatography column (Brand Catalogue No 566 14) and the filtered Luo Han extract, previously extracted in Guislin and prepared according to Section 1, percolated through the resin at ambient temperature (21±3° C.), flow controlled at 9±1 mL/min. The mogroside depleted Luo Han juice passing out of the column contained the fruit sugars, acids and minerals and was set aside for separate assessment for potential use as a base for fruit drinks.

3. Desorption, (including partial purification), of the mogrosides from the pregnant adsorbent resin by applying incrementing concentration of a food grade solvent.

Without disturbing the column packing, residual Luo Han juice was displaced from inside the resin beads with 200 mL of potable rinse water, flow 9±1 mL/min at ambient temperature.

All subsequent elution steps were conducted at the reduced flow rate of 6±1 mL/min and at ambient temperature. Each alcohol increment immediately followed the previous taking care not to let the meniscus dip into the resin bed. The ethanol concentration was adjusted according to its specific gravity measured by hydrometer.

The adsorbent resin beads were swollen and the weakly bound low molecular weight fruit phenolics eluted in two steps the first being 50 mL of 10% v/v ethanol, [specific gravity at 20° C. (s.g$^{20}$)=0.9865], then 70 mL of 20% v/v ethanol, [s.g$^{20}$ 0.9753]. These two pre-elution fractions were collected, the ethanol recovered for recycling and the residual aqueous bottoms set aside for separate assessment as a potential source of "natural" antioxidants.

The mogroside was then eluted in three steps, first in 100 mL of 35% v/v ethanol, [s.g$^{20}$ 0.9572], replaced by 100 mL of 42% v/v ethanol, [s.g$^{20}$ 0.9479] and last 100 mL of 50% v/v ethanol, [s.g$^{20}$ 0.9316]. The three mogroside rich eluents were combined and the ethanol recovered for recycling using a Rotavapor (Buchi 111) under vacuum (20-30 mm Hg) at 55° C. The aqueous residual material was dark brown in colour and slightly turbid, pH 3.3, soluble solids 5.4% w/w, Absorbance$_{420}$ 1.32. This mogroside rich mother liquor went forward to the heating step described in Section 4 below.

The adsorbent resin was subsequently regenerated with 100 mL of 80% v/v ethanol, [s.g$^{20}$ 0.8605], then rinsed with water until free of alcohol thereafter permitting its repeated re-use to harvest further batches of mogroside rich mother liquor. The ethanol was recovered for recycling and the aqueous bottoms, which contained measurable mogroside residuals, were set aside for inclusion into subsequent production cycles added back before the clarification step chronicled in Section 1.

4. Aeration and heat treatment to accelerate melanoidin development promoting agglomeration of the protein and peptide residuals in the mother liquor facilitating their subsequent adsorption by the decolourising resin.

The mogroside rich mother liquor was transferred to an open beaker which was placed in a boiling water bath. Following temperature equilibration the mother liquor was retained at >98° C. for one hour with gentle stirring and the occasional addition of aerated water to maintain a constant volume. Thereafter the thermally treated mother liquor was rapidly cooled to ambient temperature. The colour of the mother liquor had intensified and the solution was visibly turbid evidence of melanoidin formation. The visibility of the protein haze increased with cooling and it was readily filterable on No 4 filter paper (Whatman) providing an intensely browned filtrate, pH 3.3, soluble solids 5.3% w/w, Absorbance$_{420}$ 4.59.

5. Removal of the melanoidin colour (plus associated protein) developed in the mother liquor using a three stage decolourisation process incorporating inter-step pH adjustment, by contact with a US-FDA compliant decolourising resin (Alimentech A330).

Commercially available ion exchange resin (Alimentech A330) was cycled repeatedly with acidified brine (10% w/v NaCl plus 0.5% w/v HCl), water, caustic soda solution (4% w/v NaOH) and softened water in accordance with the supplier's (Bucher-Alimentech Limited) instruction until compliant with US FDA 21 CFR Ch. 1, 173.25. Thereafter 20 mL aliquots of the compliant A330 resin were transferred to three chromatography columns (Brand Catalogue No 566 32) and each regenerated with 40 mL of caustic brine, flow controlled at 1.0±0.2 mL/min, followed by 140 mL of deionised rinse water at an increased flow of 4±1 mL/min. The three columns were then joined in sequence with an inter-stage dosing and mixing pot betwixt column 1 and 2, plus another between column 2 and 3, therein permitting the controlled injection of dilute citric acid (0.1 mol/L) to maintain a pH of 3.8±0.5 in the mother liquor passing successively into decolourising columns 2 and 3.

The thermally treated and filtered mother liquor was pumped sequentially through the three decolourising columns, provisioned with inter-stage pH correction, at 2.0±0.2 mL/min followed with deionised displacement water and the light straw coloured mother liquor collected until sweetness was barely perceivable to taste. The pH of the decolourised composite was adjusted down to 3.8 with a few crystals of citric acid to obtain a pale straw coloured syrup 3.3% w/w soluble solids, Absorbance$_{420}$ 0.123. The pH adjustment was pivotal to inhibit colour reversion in the successive concentration and drying steps.

6. Concentration, drying and milling to obtain a refined bland tasting, pale coloured sweetener possessing greater than 50% w/w mogroside V content.

The decolourised and pH adjusted mother liquor was evaporated to 28% w/w soluble solids in a Rotavapor (Buchi 111) under vacuum (20-30 mm Hg) at 65° C. The remaining viscous amber liquid was transferred to a clock-glass and dried in a forced air oven (Clayson) at 65° C. for six hours.

The resulting melt was allowed to solidify at ambient temperature then hand ground with a mortar and pestle to a fine powder which was returned to the forced air oven (65° C.) and dried to constant temperature, providing off white powder, mogroside V content 54% w/w. The pH and Absorbance$_{420}$ of a 1.00% w/w solution reconstituted in deionised water was 4.0 and 0.064 respectively.

Example 2

Luo Han Guo fruit juice 4,500 L was hot water extracted from 1.2 tonne fruit using the method described in Example 1, then chill stored at 0 to −3° C. until processed. The juice was withdrawn from storage in 500 L batches and warmed in a steam jacketed open kettle to 45±5° C. The juice pH was 3.9 and availed 3.2% w/w soluble solids, (determined gravimetrically).

1. Removal of suspended solids to avert blinding of the harvesting adsorbent resin.

A proprietary pectinase enzyme preparation (Novozym 33056) 100 mL was added to each 500 L batch and the incubated mixture gently stirred for 30 minutes until a flock formed and began to settle, whereupon the temperature was rapidly raised to 85° C. to terminate the enzyme activity and pasteurise the juice. The liquid was then siphoned off into 50 L, food-grade polyethylene carboys, capped and left to cool. When below 65° C. the juice was filtered to optical clarity by pumping it through a plate filter fitted with double layers of locally purchased "filter paper" overlaid with locally procured "fine grade" diatomaceous earth. The recovery for each batch varied between 420 and 460 L, of pH 3.9, optically clear, moderately browned juice.

2. Concentration of mogrosides by harvesting onto US-FDA compliant, adsorbent resin.

100 L of commercially available divinylbenzene copolymer adsorbent resin, (Alimentech P470), was prepared for contact with food as defined in US FDA 21 CFR Ch. 1, 173.65, in a locally manufactured stainless steel chromatography column, by following the resin supplier's (Bucher-Alimentech Ltd.) instructions. Two batches of the filtered Luo Han extract, previously prepared according to Section 1, were percolated through the adsorbent resin under gravity, at 55±5° C., flow vacillating betwixt 3 and 4 L/min dependent upon the head height. The mogroside depleted Luo Han juice effused from the column to waste.

3. Desorption (including partial purification) of the mogrosides from the pregnant adsorbent resin by applying incrementing concentration of a food grade solvent.

Without disturbing the column packing, residual Luo Han juice was displaced from inside the resin beads and the column cooled with 200 L of ambient temperature potable plant water at an increased flow of 8 L/min.

All subsequent elution steps were conducted at the reduced flow rate of 6±2 L/min and at ambient temperature, (35±5° C.). Each alcoholic eluent immediately followed the previous taking care not to let the head dip into the resin bed. The recycled ethanol concentration was adjusted according to its specific gravity measured by hydrometer.

The adsorbent resin beads were swollen and the weakly bound low molecular weight fruit phenolics eluted in two steps the first being 50 L of 10% v/v ethanol, [specific gravity at 20° C. (s.g$^{20}$)=0.9865], and next 50 L of 20% v/v ethanol, [s.g$^{20}$ 0.9753]. These two pre-elution fractions were collected, the ethanol recovered for recycling and the residual aqueous bottoms discarded to waste.

The mogroside was then eluted in three steps, first in 100 L of 35% v/v ethanol, [s.g$^{20}$ 0.9572], replenished with 100 L of 42% v/v ethanol, [s.g$^{20}$ 0.9479] and last 100 L of 50% v/v ethanol, [s.g$^{20}$ 0.9316]. The three mogroside rich eluents were combined and the ethanol recovered under vacuum, for recycling employing a locally manufactured still, initial distillation temperature 65° C. ramping to 85° C.

The adsorbent resin was subsequently regenerated with 100 L of 80% v/v ethanol, [s.g$^{20}$ 0.8605], then rinsed with water until free of alcohol. The ethanol was distilled under vacuum for recycling and the aqueous bottoms, which contained measurable mogroside residuals, were returned to the beginning of the ensuing batch's clarification process, chronicled in Section 1.

In an additional step the resin was further sanitized by backwashing to fluidizing the resin then washing down-flow with 200 L of CIP solution (2% w/v caustic soda), thereafter rinsed with softened water, the residual caustic neutralised with 50 L of 4% w/v citric acid solution and finally rinsed with 500 L of potable plant water, thereby permitting the resins repeated re-use to harvest subsequent batches of mogroside rich mother liquor.

4. Heat treatment to accelerate melanoidin development promoting agglomeration of the protein and peptide residuals in the mother liquor facilitating their subsequent adsorption by the decolourising resin.

Post the alcohol recovery, the temperature of the aqueous residual 200±40 L remaining in the still was raised to 95±5° C. for one hour. The resultant intensely brown and slightly turbid mother liquor was decanted into six 50 L carboys, capped and cooled for about two hours partially immersed in cold water, where after the mother liquor temperature was determined to be below 50° C. and suitable for decolourisation.

5. Removal of the melanoidin colour (plus associated protein) developed in the mother liquor by contact with a US-FDA compliant decolourising resin, employing a two stage decolourisation process incorporating inter-stage pH adjustment.

Commercially available ion exchange resin (Alimentech A330) 25 L was transferred to each of two identical, locally made, stainless steel chromatography columns. Therein the resin was cycled twice in accordance with the resin supplier's (Bucher-Alimentech Limited) instruction applying in sequence, 50 L of caustic brine (10% w/v NaCl plus 2% w/v NaOH), followed by a softened water rinse, then 50 L of citric acid solution (4% w/v citric acid) and finally a rinse with potable plant water, thereby ensuring compliance with US FDA 21 CFR Ch. 1, 173.25. Each column of now compliant A330 resin was regenerated with 50 L of caustic brine, flow controlled at 1.0±0.1 L/min, followed by 150 L of potable plant rinse water at an increased flow of 6±1 L/min.

The thermally treated and cooled mother liquor was transferred under gravity through one of the decolourising columns, (flow 3±1 L/min), collected and pH adjusted to 3.8±0.5, then percolated through the second decolourising column, (flow correspondingly 3±1 L/min). The mother liquor remaining in the columns was recovered by flushing the columns in sequence with plant RO, (Reverse Osmosis), water. The effusing light straw coloured mother liquor was collected until sweetness was barely perceivable to taste. The pH of the decolourised composite egressing the second decolourising column was adjusted down to 3.8±0.5 with citric acid crystals to obtain a pale straw coloured syrup 300±50 L. The pH adjustment was pivotal to inhibit colour reversion in the successive concentration and drying steps.

6. Concentration and spray drying to obtain a bland tasting, pale coloured sweetener possessing greater than 35% w/w mogroside V content.

The decolourised and pH adjusted mother liquor from each batch pair was evaporated to 16-25% w/w soluble solids under vacuum (40-60 mm Hg) at 85° C. in a single stage locally constructed evaporator. The concentrates from each of the 4½ batch pairs, individual volumes 3-5 L, were accumulated frozen until sufficient bulk was available for spray drying.

Following collection of all 9 batches, the decolourised mother liquor concentrate composite was thawed and spray dried in locally manufactured equipment, providing off white powder, mogroside V content 39% w/w and accrued mogrosides 61% w/w. The pH and Absorbance$_{420}$ of a 1.00% w/w solution reconstituted in deionised water was 3.7 and 0.208 respectively.

Example 3

Luo Han Guo fruit juice 4,500 L was hot water extracted from 1.2 tonne fruit using the method described in Example 1.

1. Removal of suspended solids to avert blinding of the harvesting adsorbent resin.

The juice was filtered to optical clarity by pumping it through an ultra filtration unit with membranes having a molecular weight cut off of 100 kDa. The permeate was an optically clear, pale yellow juice.

2. Concentration of mogrosides by harvesting onto US-FDA compliant, adsorbent resin.

Commercially available divinylbenzene copolymer adsorbent resin, (Alimentech P470), was prepared for contact with food as defined in US FDA 21 CFR Ch. 1, 173.65, in a locally manufactured pressurised stainless steel column, by following the resin supplier's instructions. The filtered Luo Han extract, previously prepared according to Section 1, were pumped through the adsorbent resin under pressure at less than 50° C., flow vacillating between 30 and 50 L/min. The mogroside depleted Luo Han juice effused from the column to waste.

3. Desorption (including partial purification) of the mogrosides from the pregnant adsorbent resin by applying incrementing concentration of a food grade solvent.

Desorption of the pregnant adsorbent resin was carried out according to the process described in example 2.

4. Heat treatment to accelerate melanoidin development promoting agglomeration of the protein and peptide residuals in the mother liquor facilitating their subsequent adsorption by the decolourising resin.

Employing a locally manufactured still, the combined mogroside rich eluents from step 3 were heated to 80±5° C. for two hours. The alcohol was recovered and the resultant intensely brown and slightly turbid mother liquor was cooled for about one hour where after the mother liquor temperature was determined to be below 50° C. and suitable for decolourisation.

5. Removal of the melanoidin colour (plus associated protein) developed in the mother liquor by contact with a US-FDA compliant decolourising resin, employing a two stage decolourisation process incorporating inter-stage pH adjustment.

Decolourising of the mother liquor was carried out according to the process described in example 2.

6. Concentration and spray drying to obtain a bland tasting, pale coloured sweetener possessing greater than 35% w/w mogroside V content.

The decolourised and pH adjusted mother liquor from was evaporated to 30% w/w soluble solids under vacuum (40-60 mm Hg) at less than 70° C. in a single stage locally constructed evaporator.

Following evaporation, the decolourised mother liquor concentrate composite was spray dried in locally manufactured equipment, providing off white powder, mogroside V content 42% w/w. The Absorbance$_{420}$ of a 1.00% w/w solution reconstituted in deionised water was 0.1136.

Examples 4-7

Further sweetening compositions of the present invention were prepared using a similar method to that described in Example 1 above.

Example 8

Luo Han Guo fruit juice 142 kg was extracted from 100 kg fruit in a continuous counter current extractor having a capacity of 10 kg per hour at a temperature of 98±2° C. The juice was a light straw colour and availed 0.0% w/w soluble solids, (determined gravimetrically). This juice would be suitable as feed stock for the process outlined in example 3.

COMPARATIVE EXAMPLES

Comparative Example A

A dry sweetening composition containing mogrosides was prepared from Luo Han Guo fruit, using the method described in U.S. Pat. No. 6,124,442 (Zhou et al).

Comparative Example B

A dry sweetening composition containing mogrosides was prepared from Luo Han Guo fruit, using the following method.

Fruit is crushed/broken into irregular sizes.
The crushed fruit is fed directly into a hopper which is then filled with water. The water and fruit is then heated to 100 degrees.
Diffusion contact 40 minutes with no agitation. The liquid is filtered and pumped into a holding tank.
There are two additional extractions (each with 1.5 T of water); again the resulting liquid is filtered and stored.
The fourth (and final) extraction takes place, and after 40 minutes, the liquid is drained from the vessel.
The fruit is removed from the vessel, and the liquid from the $4^{th}$ extraction is returned to the vessel, and the next batch of fruit is added.
The supernatant is clarified by filtering, and supernatant is pumped to the absorber columns (D101 resin). These are 3 m tall and 600 mm diameter. The bed depth is approx 2.5 m, giving a bed-volume of 700 L, which is consistent with a total resin volume of ~3 $m^3$.
Elute mogroside fraction with ethanol stepwise from 10%-95%. Collect all eluant.
Distill and recover ethanol.
Pump eluted solution into the decolourising columns (AB-8 resin).
Reduce volume twenty-fold to form a concentrate.
Filter free of insoluble solids and spray dry at 50-150 deg C.

Analysis of Sweetening Compositions

The nitrogen contents of the sweetening compositions produced by the methods described in Comparative Examples A and B and Example 3 were determined using standard analytical methods: for Examples A and B: Hills labs—Catalytic Combustion (900° C., O2), separation, Thermal Conductivity Detector, [Elementar VarioMAX Analyser]; for Example 3: NZ Labs—AOAC 992.15, and are shown below:

Total nitrogen for Comparative Example A was 4.86%.
Total nitrogen for Comparative Example B was 3.54%.
Total nitrogen for Example 3 was 1.75%.

The sweetening compositions of Examples 1 to 6 and Comparative Examples A and B were analysed using high performance liquid chromatography (HPLC) to determine the percentages of both individual triterpene glycosides and total triterpene glycosides in the compositions. The HPLC method used is described separately below. The colour of the compositions was also assessed by recording the absorbance at 420 nm of a 1% w/v total solids solution of the compositions in deionised water following filtration through 0.2 μm membrane. The results of the analyses are set out in Table 1 below.

HPLC Procedure for Quantifying Mogroside V and Tentatively Identifying Seven Additional Triterpene Glycosides Found Abundant in Luo Han Guo Extract Reference: Translation of a perfunctory Chinese document co-authored by Dr Wei Ping He, (of Guilin Shili Corporation), describing in general terms the HPLC method used to quantify mogroside V at Shili. The procedure specifies a Shodex Asahipak amino column and thereby is anticipated to be an adaptation of the method developed by Dr Takekimatsuhar, (University of Dedoa, Japan), employed to prepare purified mogroside V, (a translation of which is not currently accessible).

Standards: A purified crystalline sample of mogroside V, (Certified 95.1% w/w, analysis by HPLC), isolated from Luo Han fruit, *Momordica grosvenori* Swingle, was kindly donated by Guilin Bio-GFS Company Limited. The certified (95.1 g mogroside V/100 g), material was adopted as the primary standard upon which all other tentatively diagnosed triterpene glucosides were proportioned by applying an equivalent mass extinction coefficient. [Triterpene glucosides, (other than mogroside V), were tentatively identified by their photodiode ultra-violet (UV) absorbance imprint, obtained at the apex of the eluted peak, matched against the UV fingerprint of the mogroside V standard].

Primary standard: Approximately 25 mg of dried (65° C. for 2 hours) crystalline mogroside V was accurately weighed using an analytical balance accurate to 0.1 mg.

The (23.7 mg) crystalline mogroside V was quantitatively transferred to a 50 mL volumetric flask, dissolved in 15 mL of chromatography grade methanol and made up-to 50.00 mL with 3 mM aqueous phosphoric acid. The corrected concentration of mogroside V in the resultant standard was adjusted in accordance with the proportion recorded on the certificate, (e.g., 474×0.951=450 mg/L). The resulting 450 mg/L mogroside V standard was found stable for three months when stored at ambient temperature.

Two additional standards, 50 mg/L and 200 mg/L mogroside V were prepared by serially diluting the primary standard with mobile phase "C" to permit the development of the HPLC three point calibration curve.

Detection of Mogroside V

Triterpene glucosides possess no true chromophore so quantitation utilises the inane UV absorbance attributable to the common mogroside carbon backbone, herein monitored by Chanel 1 set at 205 nm with 8 nm band width. The HPLC elution stream was additionally probed at 254 nm, 285 nm and 345 nm to invigilate the identification and purity estimation of the mogroside peaks, plus to provide a quasi classification of the prevalent non-mogroside, predominantly flavonoid peaks, absorbing strongly at the nominated wavelengths.

TABLE 1

| | Analyte | | | | | | | | |
|---|---|---|---|---|---|---|---|---|---|
| | Comparative Example A | Comparative Example B | Example 5 | Example 6 | Example 7 | Example 1 | Example 2 | Example 3 | Example 4 |
| Colour (Absorbance of a 1% w/v solution recorded at 420 nm AU | 1.064 | 0.848 | 0.510 | 0.129 | 0.189 | 0.064 | 0.208 | 0.1136 | 0.254 |
| Mogroside V % w/w[1] | 33.2 | 37.2 | 16.1 | 33.1 | 26.2 | 54.1 | 39.0 | 42.0 | 38.0 |
| Σ mogrosides % w/w[1] | 47.5 | 56.2 | 61.2 | 61.3 | 57.2 | 80.1 | 60.6 | 62.0 | 58.6 |

[1]The mogroside V and other triterpene glycoside values are presented as a weight/weight percentage all calculated as mogroside V equivalent in dried (85° C. for 2 hours) powder.

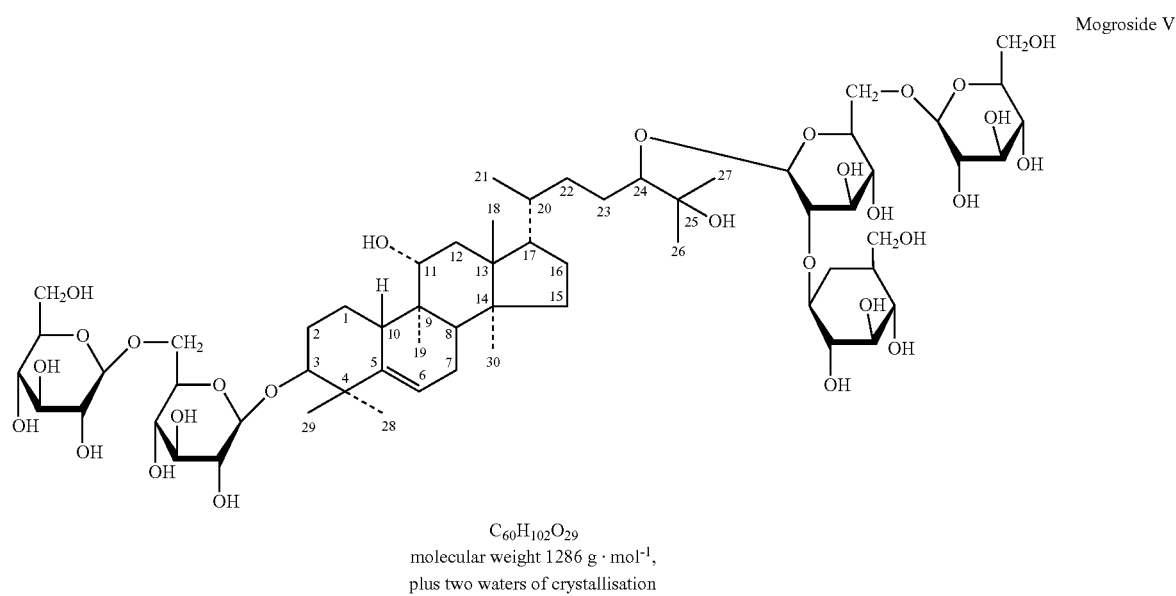

Mogroside V $C_{60}H_{102}O_{29}$
molecular weight 1286 g·mol$^{-1}$,
plus two waters of crystallisation Sample Preparation The Luo Han extract, or reconstituted concentrate, was brought to room temperature and the soluble components permitted to re-distribute from the pulp for ~2 hours with occasional agitation. Those samples with high pulp content were then centrifuged to reduce the loading onto the filtration media.

Thereafter, pulpy, or hazy extracts were filtered to optical clarity through 0.2 μm cellulose acetate membrane syringe filter equipped with a Whatman GFB depth prefilter. The initial 5 drops of filtrate were discarded as they can be depleted of the less hydrophilic mogrols due to adsorption onto the filter media. Approximately 6 mL of the subsequently filtered sample was collected for dilution to provide a mogroside V concentration of between 50 and 500 mg/L in the analysed sample directly injected into the HPLC. Any dilution was made with mobile phase "C", (defined hereinunder), and typically was 2 to 5 fold.

The clarity of the diluted filtrate was checked immediately before injection to ensure it remained optically clear as 0.2 μm filtered commercial Luo Han extract contains sufficient residual oligomeric pectates to sporadically re-haze in the dilution solvent. When necessary the injected sample was again filtered through a 4 mm diameter disposable solvent resistant (PTFE) membrane. (Extracts that are difficult to filter may require addition of filter aids. Before applying a commercial acid pectinase enzyme to reduce the viscosity and destabilise the pulp, ensure the elected enzyme preparation contains negligible side activity capable of hydrolysing glucose moieties, thereby altering the relative proportions of triterpene glycosides detected).

Instrumentation

All analyses were completed on a Shimadzu Class VP liquid chromatography unit with quaternary gradient capability and a photodiode array $D_2$ detector. The defining parameters specific to the Shimadzu apparatus are collated hereinunder.

Chromatographic Conditions for Binary Gradient Separation

Solvent A: Acetonitrile 1% by volume in water, for purging the HPLC apparatus.
Solvent B: Acetonitrile 5% by volume in aqueous phosphoric acid, 3 mMol in total solvent.
Solvent C: Acetonitrile 40% by volume in aqueous phosphoric acid, 3 mMol in total solvent.
Solvent D: Methanol 100% for wetting the reverse phase column and flushing to restoring its theoretical plate count.

All the aqueous solvents were pre-filtered through a disposable, 0.2 μm cellulose hydrophilic membrane, syringe filter, before addition to the bulk solvent carboys feeding the HPLC.

Method: Mogroside V.met
Pump: 1.0 mL/min, sum of binary gradient components.
Mixer: Static low pressure mixer with 0.5 mL hold-up volume.
Injection loop: Rheodyne 20 μL
Guard column: Re-packable, Adsorbosphere C18, 5 μm, 10 mm.
Column: Allsphere Hexyl 5 μm, C6, 4.6×250 mm.
Column oven: 35° C.
Run time: 62.05 minutes Average Retention Time and Response Factors Applied

| Compound | Retention time (min) | Window (min) | Response factor |
|---|---|---|---|
| Phenolic A | 24.2 | 2.4 | $3.48996 \times 10^{-5}$ |
| Phenolic B | 25.5 | 2.5 | $3.48996 \times 10^{-5}$ |
| Phenolic C | 26.3 | 2.6 | $3.48996 \times 10^{-5}$ |
| Triterpene glycoside I | 32.4 | 3.2 | $2.16732 \times 10^{-4}$ |
| Mogroside V | 33.3 | 3.3 | $^1 2.16732 \times 10^{-4}$ |
| Triterpene glycoside II | 34.8 | 3.5 | $2.16732 \times 10^{-4}$ |
| Triterpene glycoside III | 35.4 | 3.5 | $2.16732 \times 10^{-4}$ |
| Triterpene glycoside IV | 36.2 | 3.6 | $2.16732 \times 10^{-4}$ |
| Triterpene glycoside V | 41.1 | 4.1 | $2.16732 \times 10^{-4}$ |

-continued

| Compound | Retention time (min) | Window (min) | Response factor |
|---|---|---|---|
| Triterpene glycoside VI | 43.7 | 4.3 | $2.16732 \times 10^{-4}$ |
| Triterpene glycoside VII | 44.1 | 4.4 | $2.16732 \times 10^{-4}$ |

[1]This response factor is the average response from the three point calibration curve developed using the provided 95.1% certified mogroside V standard. The remainder of the triterpene glycoside response factors have been assigned on the premise of their exhibiting an identical mass extinction coefficient to mogroside V. The total mogrosides shown in Table 1 were also calculated using this same assumption The specific methods and compositions described herein are representative of preferred embodiments and are exemplary and not intended as limitations on the scope of the invention. Other objects, aspects and embodiments will occur to those skilled in the art upon consideration of this specification, and are encompassed within the scope and spirit of the invention. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing" etc are to be read expansively and without limitation.

The invention claimed is:

1. A process of preparing a sweetening composition containing terpene glycosides, the process comprising:
   (a) obtaining a terpene glycoside-containing liquid extract from a fresh plant source material containing terpene glycosides;
   (b) clarifying the extract;
   (c) concentrating terpene glycosides in the clarified extract to obtain a purified terpene glycoside-containing solution;
   (d) heating the purified terpene glycoside-containing solution to a sufficient temperature and for a sufficient time to form melanoidins; and
   (e) contacting the heated purified terpene glycoside-containing solution with a decolourising resin which binds melanoidins formed, thereby separating melanoidins from terpene glycosides in the solution to obtain a decolourised terpene glycoside-containing solution,
   wherein the decolourising resin comprises an anion resin regenerated in a chloride form, and
   wherein a filtered (0.2 µm) decolourised terpene glycoside-containing solution in water having a solids content of 1% w/v has an absorbance at 420 nm about 0.55 or below.

2. The process according to claim 1, wherein the fresh plant source material is Luo Han Guo fruit.

3. The process according to claim 1, wherein step (a) comprises contacting macerated Luo Han Guo fruit with hot water, at a sufficient time and for a sufficient temperature to extract triterpene glycosides from the fruit.

4. The process according to claim 3, wherein the extraction is carried out using counter current extraction.

5. The process according to claim 1, wherein the clarification step (b) comprises ultrafiltration of the extract.

6. The process according to claim 1, wherein the decolourising resin used in step (e) comprises a highly porous, macroporous, type I, strongly basic anion resin.

7. A process of preparing a sweetening composition from a fresh plant source material containing terpene glycosides, wherein the process comprises:
   (a) heating a terpene glycoside-containing solution obtained by extracting terpene glycosides from the plant source material to a sufficient temperature and for a sufficient time to form melanoidins; and
   (b) contacting the heated terpene glycoside-containing solution with a decolourising resin which binds melanoidins formed, thereby separating melanoidins from the terpene glycosides in the solution to obtain a decolourised terpene glycoside-containing solution,
   wherein the decolourising resin comprises an anion resin regenerated in a chloride form, and wherein a filtered (0.2 µm) decolourised terpene glycoside-containing solution in water having a solids content of 1% w/v has an absorbance at 420 nm about 0.55 or below.

8. The process of claim 1, wherein the decolourised terpene glycoside-containing solution comprises about 16% to about 75% mogroside V, on a dry weight basis.

9. The process of claim 7, wherein the decolourised terpene glycoside-containing solution comprises about 16% to about 75% mogroside V, on a dry weight basis.

10. The process of claim 1, wherein the decolourised terpene glycoside-containing solution comprises about 30% to about 95% terpene glycosides, on a dry weight basis.

11. The process of claim 7, wherein the decolourised terpene glycoside-containing solution comprises about 30% to about 95% terpene glycosides, on a dry weight basis.

12. The process of claim 1, wherein a filtered (0.2 µm) decolourised terpene glycoside-containing solution in water having a solids content of 1% w/v has an absorbance at 420 nm less than about 0.5.

13. The process of claim 7, wherein a filtered (0.2 µm) decolourised terpene glycoside-containing solution in water having a solids content of 1% w/v has an absorbance at 420 nm less than about 0.5.

14. A process of preparing a sweetening composition from a fresh plant source material containing terpene glycosides, wherein the process comprises:
   (a) extracting terpene glycosides from the fresh plant source material to produce a terpene glycoside-containing liquid extract;
   (b) heating the extract to a sufficient temperature and for a sufficient time to form melanoidins;
   (c) providing a decolourising resin;
   (d) regenerating the decolourising resin in a chloride form; and
   (e) contacting the heated extract from step (b) with the decolourising resin from step (d) which binds melanoidins formed, thereby separating melanoidins from the terpene glycosides in the extract to obtain a decolourised terpene glycoside-containing solution,
   wherein the decolourising resin comprises an anion resin regenerated in a chloride form, and wherein a filtered (0.2 µm) decolourised terpene glycoside-containing solution in water having a solids content of 1% w/v has an absorbance at 420 nm about 0.55 or below.

15. The process of claim 14, wherein a filtered (0.2 µm) decolourised terpene glycoside-containing solution in water having a solids content of 1% w/v has an absorbance at 420 nm less than about 0.5.

16. The process of claim 14, wherein the decolourised terpene glycoside-containing solution comprises about 16% to about 75% mogroside V, on a dry weight basis.

17. The process of claim 14, wherein the decolourised terpene glycoside-containing solution comprises about 30% to about 95% terpene glycosides, on a dry weight basis.

* * * * *